(12) United States Patent
Madrid

(10) Patent No.: US 10,889,311 B2
(45) Date of Patent: Jan. 12, 2021

(54) MEDICAL INSTRUMENTS STROLLER

(71) Applicant: Steve Madrid, Lubbock, TX (US)

(72) Inventor: Steve Madrid, Lubbock, TX (US)

(*) Notice: Subject to any disclaimer, the term of this patent is extended or adjusted under 35 U.S.C. 154(b) by 0 days.

(21) Appl. No.: 16/407,506

(22) Filed: May 9, 2019

(65) Prior Publication Data

US 2019/0263433 A1 Aug. 29, 2019

(51) Int. Cl.
| | |
|---|---|
| *B62B 1/00* | (2006.01) |
| *B62B 1/26* | (2006.01) |
| *A61B 50/36* | (2016.01) |
| *A61B 50/13* | (2016.01) |
| *A61B 50/20* | (2016.01) |
| *A61B 50/30* | (2016.01) |

(52) U.S. Cl.
CPC .............. *B62B 1/008* (2013.01); *A61B 50/13* (2016.02); *A61B 50/20* (2016.02); *A61B 50/362* (2016.02); *B62B 1/26* (2013.01); *A61B 2050/314* (2016.02)

(58) Field of Classification Search
CPC ........... B62B 1/20; B62B 1/208; B62B 1/008; A61B 50/13; A61B 50/20; A61B 50/24; A61B 50/362; A61B 50/30; A61B 50/31; A61B 2050/311; A61B 2050/314; A61B 2050/318
See application file for complete search history.

(56) References Cited

U.S. PATENT DOCUMENTS

| | | | | |
|---|---|---|---|---|
| 6,139,164 | A * | 10/2000 | Bolta .................. | F21L 14/04 248/454 |
| 6,149,168 | A * | 11/2000 | Pauser ................. | B25H 3/00 280/43.1 |
| 7,445,216 | B1 * | 11/2008 | Chou .................. | B62B 1/142 280/40 |
| 7,997,594 | B1 * | 8/2011 | Mortazavi ............ | B62B 1/008 206/315.9 |
| 8,746,711 | B1 * | 6/2014 | Jarma ................. | B62B 1/008 280/47.131 |
| 2001/0000901 | A1 * | 5/2001 | Kambouris .......... | G06F 1/1626 220/212 |
| 2006/0027999 | A1 * | 2/2006 | Hardin ................ | A45C 13/385 280/646 |
| 2007/0273114 | A1 * | 11/2007 | Katz .................. | B62B 1/12 280/47.18 |

(Continued)

*Primary Examiner* — Brian L Swenson
(74) *Attorney, Agent, or Firm* — Barry Choobin; Patent 360

(57) ABSTRACT

The present invention is directed to a medical instrument stroller having a tubular wedge-shaped collapsible frame structure. The frame is having a first frame member and a second frame member, the first frame member is pivotally coupled to the second frame member. A pair of wheels is coupled to the first frame member. A receptacle having a proximal end and a distal end, the proximal end of the receptacle is pivotally coupled to the second frame member while the distal end of the receptacle is coupled to an attachment member. The attachment member is coupled to the first frame member and is configured to allow the receptacle to switch between a horizontal position and a vertical stowed position. An interchangeable toolbox is mounted on the receptacle. A disposable sharps box is mounted to a support member that extends between legs of the second frame member. Additionally, a trash collector bag is coupled to the receptacle.

13 Claims, 4 Drawing Sheets

(56) References Cited

U.S. PATENT DOCUMENTS

| | | | |
|---|---|---|---|
| 2009/0127829 A1* | 5/2009 | Thomas | B62B 1/14 280/652 |
| 2010/0007250 A1* | 1/2010 | Sharpe | A61G 12/001 312/209 |
| 2011/0068562 A1* | 3/2011 | Keffeler | A61G 12/001 280/651 |
| 2014/0210172 A1* | 7/2014 | Lurie | B62B 1/262 280/47.24 |
| 2015/0305086 A1* | 10/2015 | Uttley | B62B 3/02 280/652 |
| 2016/0157951 A1* | 6/2016 | Schoenig | A61G 7/0503 280/830 |
| 2016/0346056 A1* | 12/2016 | Demers | A61M 16/021 |
| 2018/0242888 A1* | 8/2018 | Schmutzer | A61B 5/1112 |
| 2019/0105120 A1* | 4/2019 | Norman | G01G 17/00 |

* cited by examiner

MEDICAL INSTRUMENTS STROLLER

BACKGROUND

Technical Field of Invention

The embodiments herein generally relate to medical instrument trolleys used in hospitals, clinics, operation theatres, etc. The embodiments herein more particularly relate to a medical instrument stroller having a unique and simple design assembly intended for accommodation and transportation of medical devices/equipments/tools in hospitals.

DESCRIPTION OF RELATED ART

Medical equipment, also known as armamentarium, is designed to aid in the diagnosis, monitoring or treatment of medical conditions. Medical tools are the tools used by doctors, surgeons, physicians, etc. for diagnosing the patients. There are various types of tools used in operation theatres for conducting a surgery or operation. The various medical tools include syringes, sample collecting containers, cotton balls and swabs, suturing materials, masks and gloves, sterilizing solution, glucometers, thermometers, otoscopes, ear scopes, surgical instruments (scalpels, forceps, hemostats and needle holder).

Medical equipment vehicles/trolleys/carts are being used by doctors and nurses in routine medical care. These medical equipment trolleys are used to keep surgical instruments and other essential accessories handy while carrying out the various medical practices.

U.S. Pat. No. 5,083,805 provides an equipment trolley, particularly for transporting and/or holding medical instruments, equipment and the like, can, by using standardized components such as carrier trays, drawer blocks.

Chinese patent CN203408110 provides a medical equipment trolley, which comprises a floor rack and a medical equipment fixing seat arranged at the top of the floor rack, wherein the medical equipment fixing seat comprises a substrate and a plurality of movable baffle plates connected to the substrate in a sliding way; a first locking part is arranged on each movable baffle plate, and can be used for fixing the movable baffle plate and the substrate; the movable baffle plates enclose a medical equipment accommodation space which can be enlarged or reduced along with the movement of the movable baffle plates.

Russian patent RU124878 provides trolley for placement of medical equipment comprises equipped with wheels of a tubular metal frame comprising a horizontal U-shaped base with an arcuate front part, the sides of which is attached an inclined rack, made in the form of two curved bars, the U-shaped base and the inclined desk tubular metal frame implemented with antibacterial coating based on a powder paint with antimicrobial additives containing silver nanoparticles or silver ions.

US patent application US20150232113 provides an equipment carrier includes a surface module with a first securing device and a column module with a second securing device. The first securing device on the surface module and the second securing device on the column module are designed corresponding to each other such that the column module and the surface module can be connected to each other with a first, linear movement and a subsequent second, rotational movement of the column module relative to the surface module.

However, these mentioned medical equipment trolleys/stroller, have drawback of cumbersome design assembly and poor versatility. Most of these products are heavy weight and require a large amount of space.

Hence there is a need to develop a portable and light weight trolley/stroller for keeping medical tools and other medical accessories handy.

The above mentioned shortcomings, disadvantages and problems are addressed herein, as detailed below.

SUMMARY OF THE INVENTION

The primary object of the embodiments herein is to provide a medical instrument stroller that is lightweight, collapsible and free-standing.

Another object of the embodiments herein is to provide a medical instrument stroller for phlebotomy/medical toolbox that runs on two smooth-running quiet wheels.

Yet another object of the embodiments herein is to provide a medical instrument stroller that is safe, light, organized, collapsible and mobile work station used for light tools to perform their duties in Direct Patient Care.

Yet another object of the embodiments herein is to provide a medical instrument stroller that is lighter and easier to manoeuvre.

According to the embodiments herein, a medical instrument stroller is provided. The medical instrument stroller comprises a tubular wedge-shaped collapsible frame structure having at least one pair of wheels, an interchangeable tool box conveniently placed between the wedge-shaped frame structure on a receptacle, a trash collector and a disposable sharps box.

According to an embodiment herein, the tool box is openable from top.

According to an embodiment herein, the tool box comprises a flap. The flap is opened when lifted.

According to an embodiment herein, the tool box is interchangeable as the flap forms a convenient table top when in a closed position and acts as a clipboard for organizing paperwork, tools and labelling patient specimens when in an opened position.

According to an embodiment herein, the pair of wheels is present on a posterior bottom side of the wedge-shaped frame.

According to an embodiment herein, the pair of wheels enable the stroller to a "Lean and Lock" movement.

According to an embodiment herein, the trash collector comprises a trash bag neatly tuck into a folded unit for sleek mobility.

According to an embodiment herein, the stroller has a two-wheel lightweight design which enables a "tight turn ratio" of the stroller.

According to an embodiment herein, the stroller weighs in a range of 17-25 lbs.

According to an embodiment herein, the stroller takes up at least two square feet of floor space when collapsed and standing upright on its' own.

According to an embodiment herein, the stroller takes at least four square feet of floor space when extended and being utilized for patient care.

According to an embodiment herein, the tool box is removable.

According to an embodiment herein, the tool box is fixed permanently to the frame structure.

According to an embodiment herein, the stroller runs on a single pair of wheels.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

DETAILED DESCRIPTION OF THE DRAWINGS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a lightweight, free-standing, collapsible medical instrument trolley in the form of a stroller. The medical instrument stroller is to be used in hospitals, operation theatres, clinics, phlebotomy, etc. A medical toolbox is conveniently placed on a wedge-shaped tubular and collapsible frame structure which runs on at least one pair of smooth-running quiet wheels. The medical instrument stroller has a conveniently attached sharps box and a trash receptacle. The medical instrument stroller is beneficial for phlebotomists, hospital nurses, home health nurses, emergency medical personnel and any other medical clinicians who need a safe, light, organized, collapsible and mobile work station for light tools to perform their duties in direct patient care.

Figure 1:
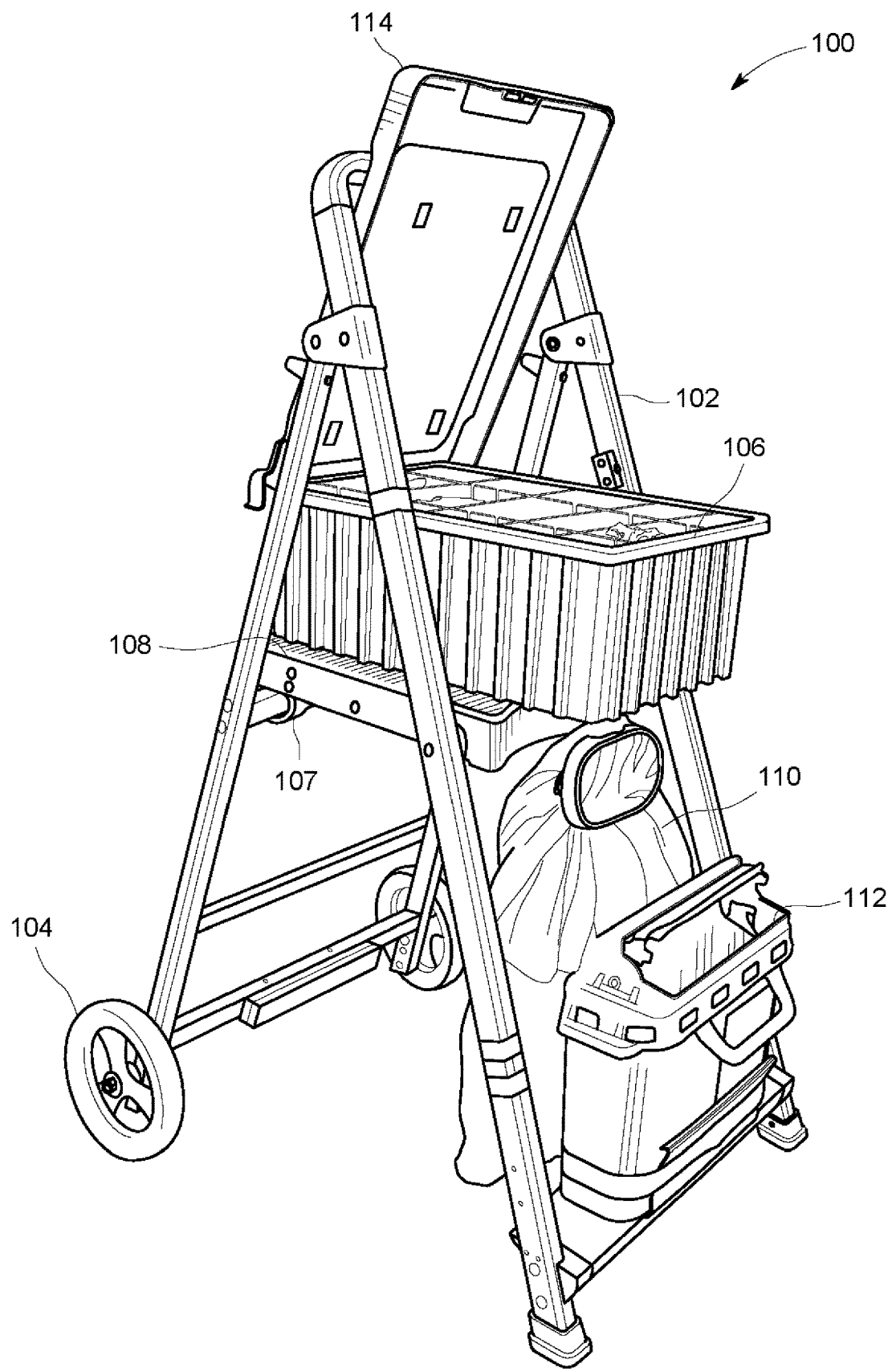
FIG. 1 is an isometric view of a medical instrument stroller, according to an embodiment herein.
Figure 3:
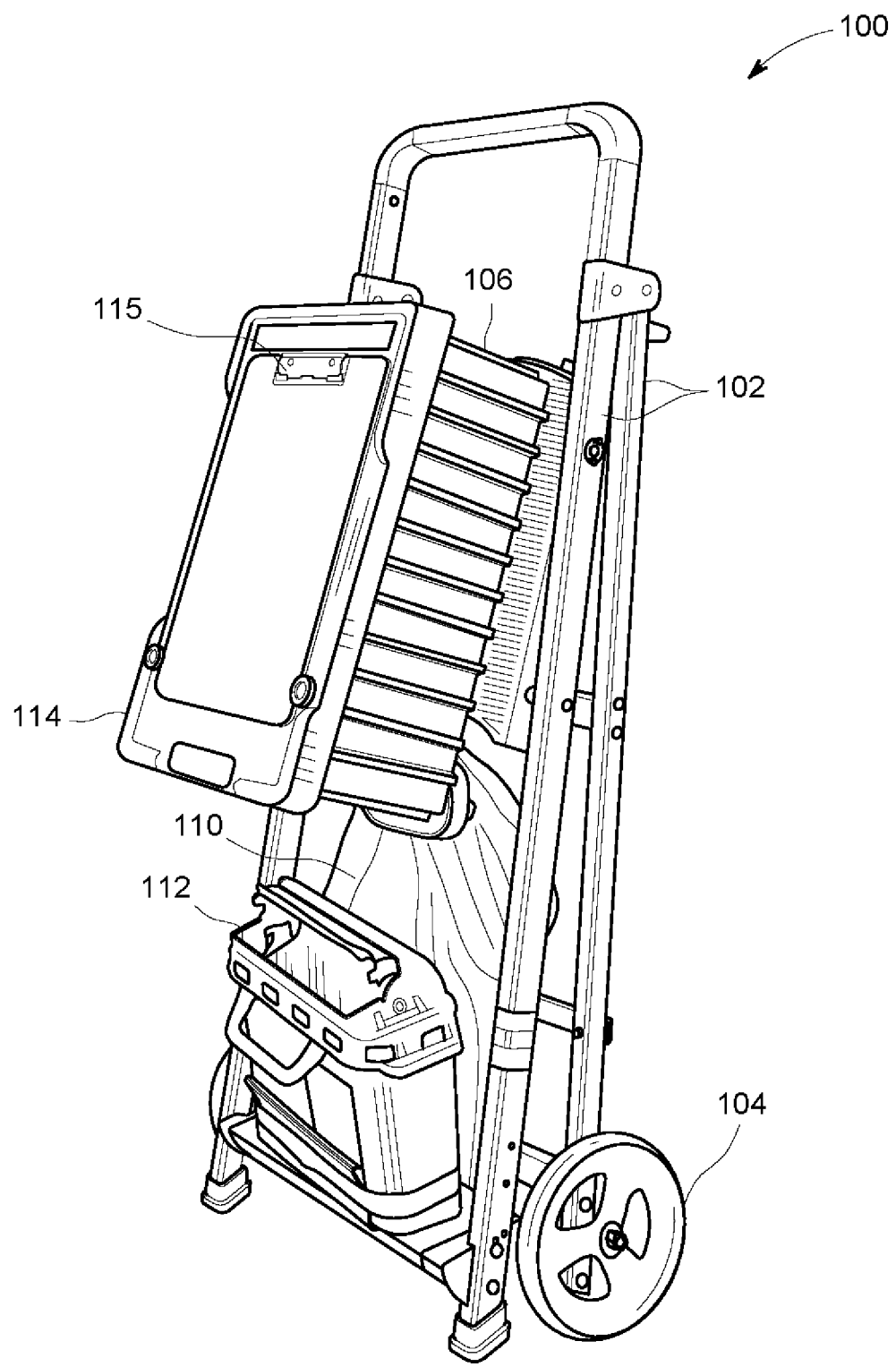
FIG. 3 shows an isometric view of the medical instrument stroller in a closed position standing upright, according to an embodiment herein.

FIG. 1 is an isometric view of the medical instrument stroller, according to an embodiment herein. With respect to FIG. 1, the medical instrument stroller 100 comprises a tubular wedge-shaped collapsible frame structure 102 having a first frame member and a second frame member, the first frame member pivotally coupled to the second frame member. The first frame member having at least one pair of wheels 104. The medical instrument stroller 100 further includes an interchangeable tool box 106 conveniently placed between the wedge-shaped frame structure on a receptacle 108, a trash collector 110, and a disposable sharps box 112. The tool box is openable from top. The flap 114 is openable when lifted. The flap 114 forms a table top when in closed position. Thus, the tool box 106 is interchangeable as the flap 114 forms a convenient table top when in closed position or as a clipboard for organizing paperwork, tools and labelling patient specimens when opened. The spacious and interchangeable tool box 106 is securely attached to the light and tubular wedge-shaped collapsible frame structure 102 on a receptacle 108. The receptacle 108 having a proximal end and a distal end, the proximal end pivotally coupled to the second frame member and the distal end of the receptacle 108 is coupled to an attachment member 107 that is coupled to the first frame member. The attachment member 107 allows the receptacle to switch between a horizontal position as shown in FIG. 1 and a vertical stowed position as shown in FIG. 3. According to an embodiment herein, the tool box 106 is removable. According to another embodiment herein, the tool box 106 is fixed permanently to the frame structure 102. Moreover, the tool box 106 is fixed to the receptacle 108 via screws.

The wedge-shaped frame structure 102 is wide open at the bottom side and narrow towards an upward direction. The pair of wheels 104 is present on a posterior bottom side of the wedge-shaped frame. This enables the stroller 100 to a "Lean and Lock" movement. The stroller stands by itself at the time of work, but when leaned and locked, it closes itself, particularly saving space and making it easier to store and to be non-intrusive when out in the field. The wheels are smooth and quite running wheels movable in all directions. The stroller runs on this single pair of wheels. In order to move the stroller, the stroller is slightly bent downwardly and moved forward. The stroller has a two-wheel lightweight design which enables a "tight turn ratio" of the stroller.

The trash collector 110 comprises a trash bag neatly tuck into a folded unit for sleek mobility. The trash collector 110 is present on the anterior bottom side of the stroller in between the wedge-shaped frame structure 102. The trash collector 110 is replaceable.

The disposable sharps box 112 is present in front of the trash collector 110 at the anterior bottom side of the stroller. The disposable sharps box 112 is also replaceable. A sharps container is a hard-plastic container that is used to safely dispose of hypodermic needles and other sharp medical instruments, such as an IV catheters and disposable scalpels.

Figure 2:
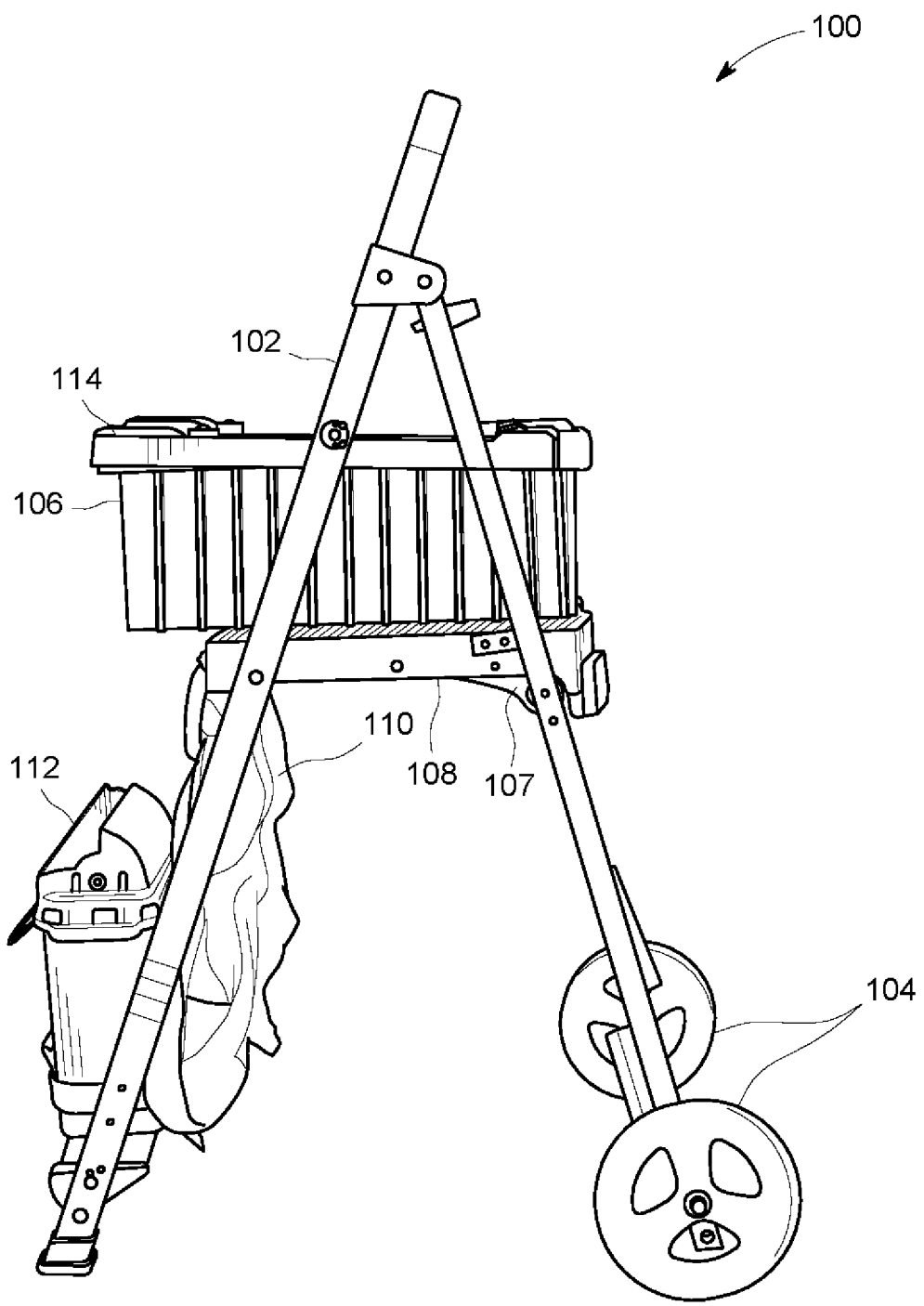
FIG. 2 shows a side view of the medical instrument stroller, according to an embodiment herein.

FIG. 2 shows a side view of the medical instrument stroller, according to an embodiment herein. With respect to FIG. 2, the lightweight, free-standing, collapsible medical instrument trolley in the form of a stroller is shown. The medical toolbox is conveniently placed on a wedge-shaped tubular and collapsible frame structure which runs on at least one pair of smooth-running quiet wheels. The medical instrument stroller has a conveniently attached sharps box and a trash receptacle.

FIG. 3 shows an isometric view of the medical instrument stroller in a closed position standing upright, according to an embodiment herein. With respect to FIG. 3, the stroller takes up at least two square feet of floor space when collapsed and standing upright on its' own. The tool box collapses down in a vertical stowed position. FIG. 3 further shows a clip 115 mounted on the outer surface of the flap 114. The clip 115 can be used to releasably bind a set of papers.

Figure 4:
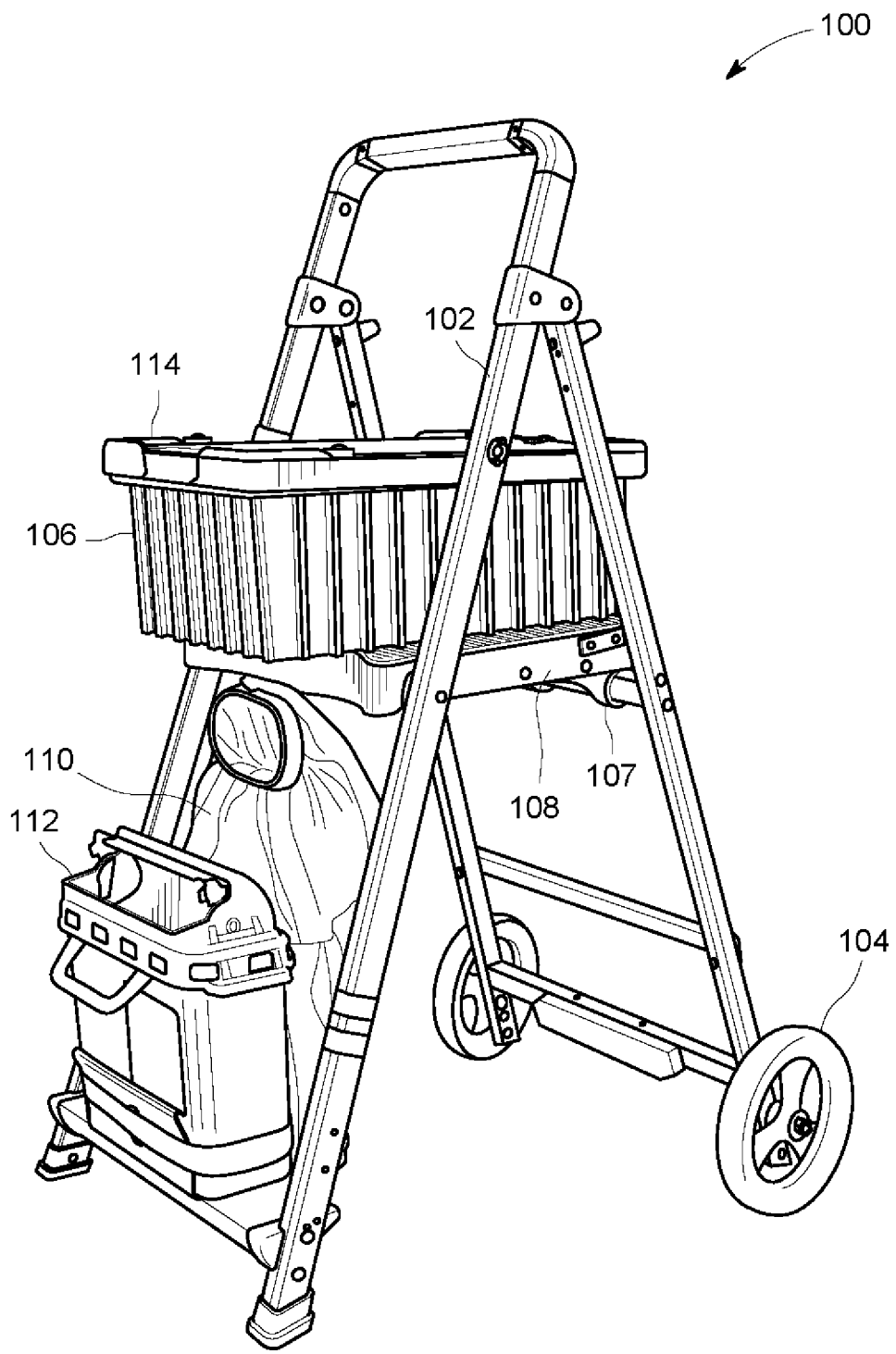
FIG. 4 shows an isometric view of the medical instrument stroller showing an interchangeable tool box conveniently placed between the wedge-shaped frame structure on a receptacle, according to an embodiment herein.

FIG. 4 shows an isometric view of the medical instrument stroller showing the interchangeable tool box conveniently placed between the wedge-shaped frame structure on a receptacle, according to an embodiment herein. With respect to FIG. 4, the tool box is interchangeable as the flap 114 forms a convenient table top when in closed position or as a clipboard for organizing paperwork, tools and labelling patient specimens when opened.

According to an embodiment, the stroller weighs in a range of 17-25 lbs.

According to an embodiment, the stroller takes up at least two square feet of floor space when collapsed and standing upright on its' own. According to an embodiment, the stroller takes at least four square feet of floor space when extended and being utilized for patient care.

The medical instrument stroller according to the embodiments herein is lighter and easier to maneuver than other medical carts in the market. Its' unique lightweight and two-wheel design enable its' tight turn ratio. Its' lightweight and collapsibility make it ideal for transport in vehicles when in transit from one location to another.

The medical instrument stroller has an elegant design consisting of a roomy, versatile, interchangeable medical storage box to organize light medical tools, equipment and patient specimens while performing medical procedures on patients. Phlebotomy tools and supplies for Lab work, tools and supplies for nurses' use, tools and supplies that emergency medical personnel are better utilized with the medical instrument stroller.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims.

I claim:

1. A medical instrument stroller, comprising:
   a tubular wedge-shaped collapsible frame structure having a first frame member and a second frame member, the first frame member having a proximal end and a distal end, the second frame member having a proximal end and a distal end, a joint member coupled to near the proximal end of the second frame member, the proximal end of the first frame member is pivotally coupled to the joint member, the joint member configured to limit movement of the first frame member up to a predetermined range relative to the second frame member, the first frame member having a first leg and a second leg running parallel to each other, the second frame member having a third leg and a fourth leg running parallel to each other, the distal end of the first frame member having at least one pair of wheels, each of the at least one pair of wheels coupled to the first leg and the second leg;
   a receptacle having a proximal end and a distal end, the proximal end of the receptacle pivotally coupled to the second frame member between the third leg and the fourth leg, the distal end of the receptacle coupled to an attachment member, wherein the attachment member is coupled to a bar extending between the first leg and the second leg of the first frame member, the attachment member configured to permit the receptacle to switch between a horizontal position and a vertical stowed position;
   an interchangeable tool box mounted on the receptacle;
   a trash collector bag; and
   a disposable sharps box coupled to a support member that extends between the third leg and the fourth leg of the second frame member near its distal end.

2. The stroller according to claim 1, wherein the tool box is open at top.

3. The stroller according to claim 2, wherein the tool box comprises a flap configured to close the open top, the flap pivotally coupled to an edge of the open top.

4. The stroller according to claim 3, wherein the flap further comprises a clip coupled to an outer surface of the flap for releasably binding a set of papers.

5. The stroller according to claim 1, wherein the pair of wheels enable a lean and lock configuration for the stroller.

6. The stroller according to claim 1, wherein the trash collector bag is having a mouth and a body, the trash collector bag along its mouth is coupled to the proximal end of the receptacle.

7. The stroller according to claim 1, wherein the stroller has a two-wheel lightweight design which enables a tight turn ratio of the stroller.

8. The stroller according to claim 1, wherein the stroller weighs in a range of 17-25 lbs.

9. The stroller according to claim 1, wherein the stroller takes up at least two square feet of floor space when collapsed and standing upright on its own.

10. The stroller according to claim 1, wherein the stroller takes at least four square feet of floor space when extended and being utilized for patient care.

11. The stroller according to claim 1, wherein the tool box is removable.

12. The stroller according to claim 1, wherein the tool box is fixed permanently to the frame structure.

13. The stroller according to claim 1, wherein the stroller comprises a single pair of wheels.

\* \* \* \* \*